United States Patent [19]
Radisch, Jr.

[11] Patent Number: 5,742,019
[45] Date of Patent: Apr. 21, 1998

[54] METHOD FOR MANUFACTURING AN ATHERECTOMY CUTTER HAVING A POSITIVE ANGLE OF ATTACK

[75] Inventor: Herbert R. Radisch, Jr., San Diego, Calif.

[73] Assignee: InterVentional Technologies Inc., San Diego, Calif.

[21] Appl. No.: 546,676

[22] Filed: Oct. 23, 1995

Related U.S. Application Data

[63] Continuation-in-part of Ser. No. 368,698, Jan. 3, 1995, abandoned, which is a continuation of Ser. No. 136,561, Oct. 12, 1993, abandoned, which is a continuation of Ser. No. 820,748, Jan. 13, 1992, abandoned.

[51] Int. Cl.⁶ .................................................. B23H 9/00
[52] U.S. Cl. .............................. 219/69.17; 76/104.1
[58] Field of Search ................... 76/104.1; 219/69.17; 606/159

[56] References Cited

U.S. PATENT DOCUMENTS

| | | |
|---|---|---|
| 2,729,210 | 1/1956 | Spencer . |
| 2,730,101 | 1/1956 | Hoffman . |
| 3,815,604 | 6/1974 | O'Malley et al. . |
| 4,134,807 | 1/1979 | Briffod .................................. 219/69.17 |
| 4,445,509 | 5/1984 | Auth . |
| 4,490,600 | 12/1984 | Rae ....................................... 219/69.17 |
| 4,598,710 | 7/1986 | Kleinberg et al. . |
| 4,640,296 | 2/1987 | Schnepp-Pesch et al. . |
| 4,886,061 | 12/1989 | Fischell et al. . |
| 4,887,613 | 12/1989 | Farr et al. . |
| 4,895,166 | 1/1990 | Farr et al. . |
| 4,958,539 | 9/1990 | Stasz et al. ............................. 76/104.1 |
| 4,966,604 | 10/1990 | Reiss . |
| 5,014,421 | 5/1991 | Swarden et al. ....................... 219/69.17 |
| 5,019,088 | 5/1991 | Farr . |
| 5,395,311 | 3/1995 | Andrews ................................. 606/159 |
| 5,556,408 | 9/1996 | Farhat ..................................... 606/159 |

*Primary Examiner*—Geoffrey S. Evans
*Attorney, Agent, or Firm*—Nydegger & Associates

[57] ABSTRACT

A method for manufacturing an atherectomy cutter having a positive angle of attack which includes the following steps: forming a rod having a longitudinal axis into a cutter blank having a first cylindrical section, a second cylindrical section, and a uniformly tapered section therebetween; boring an axial passageway through the cutter blank to create walls of substantially similar thickness in each section of the cutter blank; grinding a pair of diametrically opposed flats on the external surface of the uniformly tapered section of the cutter blank; and removing the wall portions of the tapered section between the flats to create a pair of blades.

15 Claims, 3 Drawing Sheets

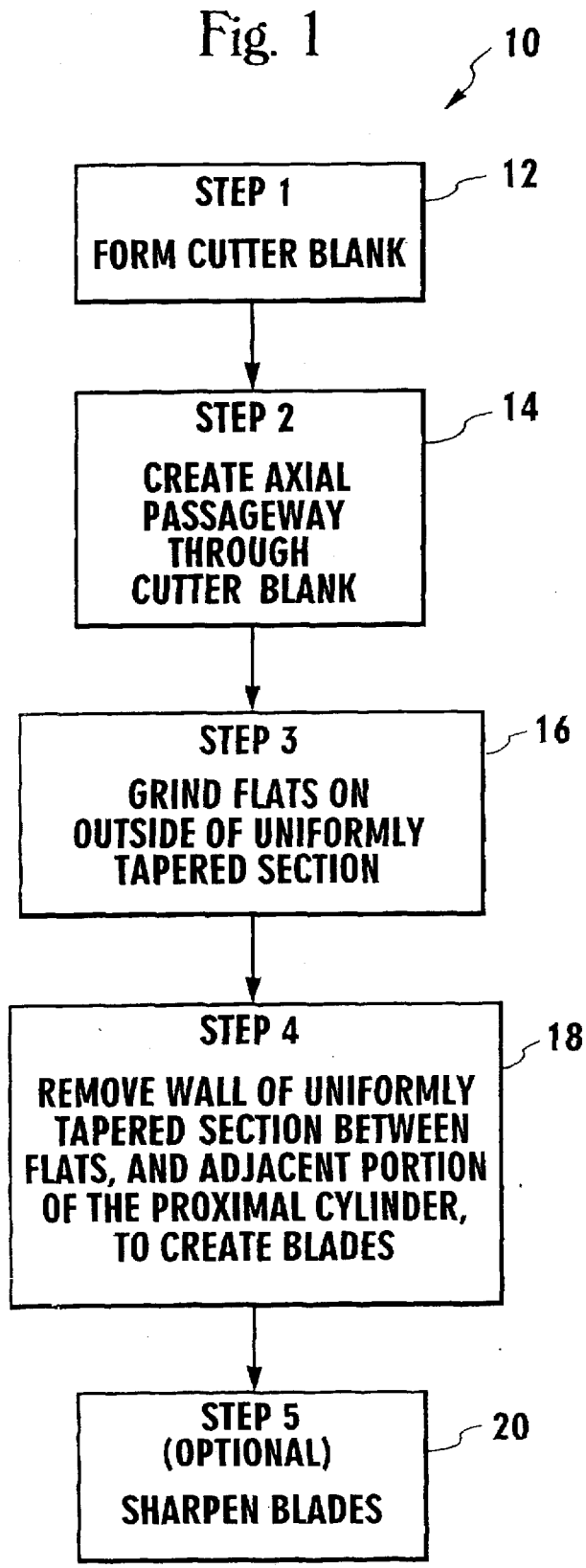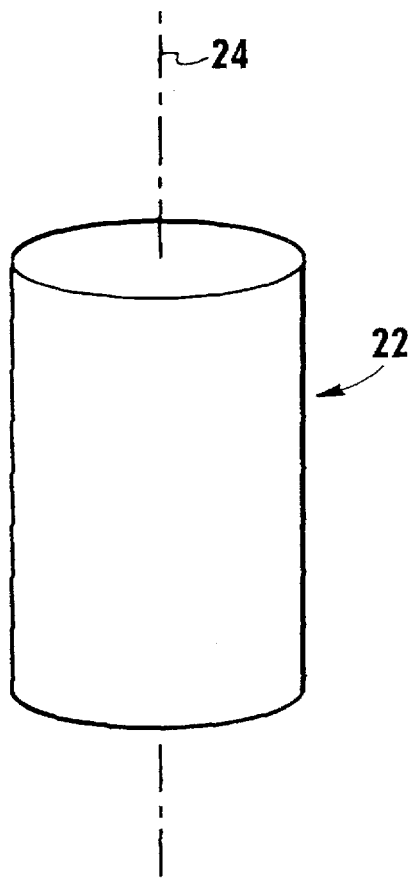

Fig. 7
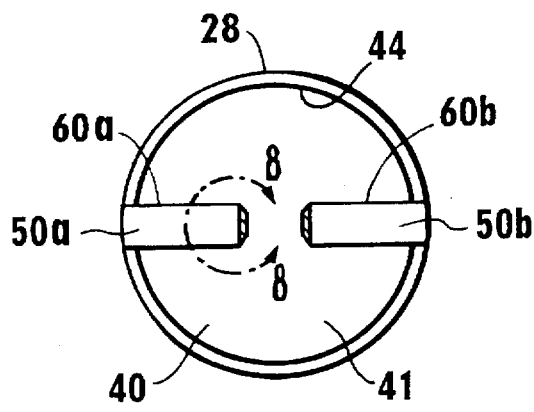
Fig. 8
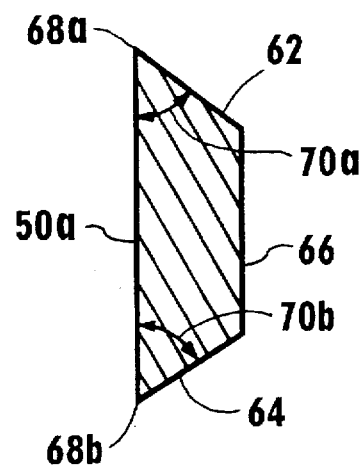
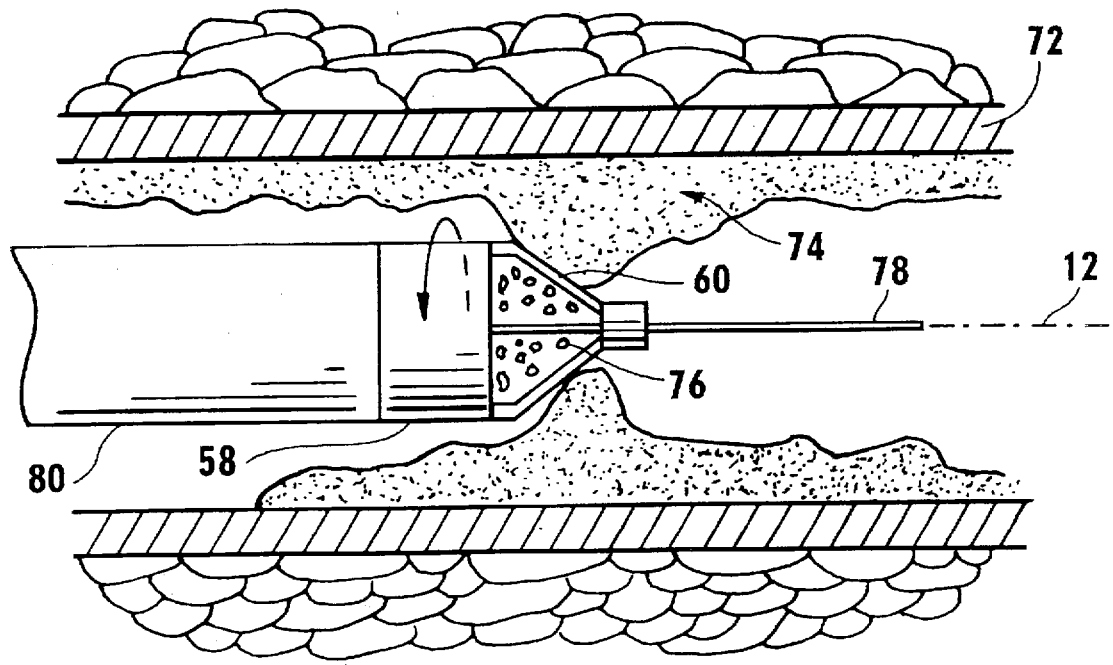
Fig. 9

5,742,019

METHOD FOR MANUFACTURING AN ATHERECTOMY CUTTER HAVING A POSITIVE ANGLE OF ATTACK

RELATED APPLICATIONS

This is a continuation-in-part patent application of co-pending U.S. patent application Ser. No. 08/368,698, filed on Jan. 3, 1995, now abandoned, and entitled "Atherectomy Cutter with a Positive Attack Angle," which is a continuation patent application of U.S. patent application Ser. No. 08/136,561, filed Oct. 12, 1993, now abandoned, and entitled "Atherectomy Cutter with a Positive Attack Angle" which is a continuation patent application of U.S. patent application Ser. No. 07/820,748, now abandoned, filed on Jan. 13, 1992, and entitled "Atherectomy Cutter with a Positive Attack Angle."

FIELD OF INVENTION

The present invention relates generally to medical devices. More particularly, the present invention relates to medical devices which are insertable into the body. Even more particularly, the present invention relates to the manufacturing of such medical devices. The present invention is most particularly, though not exclusively, useful for the manufacturing of an atherectomy cutter.

BACKGROUND OF INVENTION

The collection or formation of plaque on the inside surface of the arteries, called stenoses, presents a significant health concern to humans. More specifically, the presence of a stenosis may partially, or even totally, restrict the blood flow through the artery. The consequences of such restriction may vary, but in severe instances, stenoses can cause heart attacks, strokes, or deterioration of tissue which is dependent on the blood supplied from the restricted artery.

Because of the extreme dangers associated with the presence of stenoses, several methods of treatment have been developed to alleviate the effects of stenotic blockages. For example, open heart surgery has long been used to surgically remove the restricted section of an artery in order to restore blood flow through the artery. While effective, open heart surgery is highly invasive and very traumatic to the patient. Consequently, open heart surgery poses a significant risk to the patient, including the possibility of severe infection or even death.

Another method for treating stenoses is what is referred to in the medical field as an angioplasty procedure. In such a procedure, a deflated angioplasty balloon is inserted into an artery and guided to the location of a stenotic blockage. Upon proper positioning of the balloon across the stenosis, the balloon is inflated to displace the stenosis and dilate the artery sufficiently to restore the blood flow therethrough. Following the dilation of the artery, the angioplasty balloon is deflated and removed. Although angioplasty is significantly less traumatic than open-heart surgery, an angioplasty procedure is not without risks. This is so, due to the presence of the plaque which was displaced by the balloon during dilation, but which still remains in the artery. In sum, this plaque presents an increased risk of a future restenosis at the same location in the artery. Further, there are additional risks caused by an angioplasty procedure. More specifically, with the dilation of the artery using an angioplasty balloon, it is possible that the arterial walls could weaken, or even burst, under exposure to the pressure necessary for dilation.

Yet another, more recently developed, method of treating a stenosis is the atherectomy procedure. Such a procedure is set forth in U.S. Pat. No. 4,895,166, which issued to Farr, et. al. for an invention entitled "Rotatable Cutter For The Lumen Of A Blood Vessel." As disclosed by Farr, an atherectomy procedure involves the insertion of an atherectomy cutter into a restricted artery. Following the positioning of the cutter at the stenosis within the artery, the cutter is rotated such that the blades of the cutter strike the stenosis. By continually rotating the atherectomy cutter while advancing it through the stenotic blockage, the stenosis is cut away and a passageway is created through the blockage thereby restoring the flow of blood through the artery. Additionally, the recently detached stenotic particles may be removed from the artery using an external suction device connected, via a torque tube, to the center of the cutter. Thus, a significant advantage of the atherectomy procedure is that the stenosis is physically cut from the arterial wall and removed from the body, unlike the angioplasty procedure, where the stenosis is merely displaced against the arterial wall.

Overall, the atherectomy procedure has enjoyed widespread acceptance as an alternative procedure for use in the treatment of stenoses. In fact, the atherectomy procedure has gradually become the procedure of preference for use in such treatment. Previously available atherectomy cutters, however, have had some characteristics which can limit their effectiveness in removing stenoses. More specifically, the atherectomy cutters previously available have cutter blades with curved outer surfaces that conform to the rotational path of the cutter. Because the outer surface of the cutter blade is curved, the angle at which the blade strikes the stenosis, when the cutter is rotated, is small. This angle, commonly referred to as the angle of attack, is particularly small in instances where the stenosis is pliable. In fact, the angle of attack may approach zero, and thereby effectively produce no cutting action. Thus, by creating a cutter blade with a planar, rather than a curved, outer surface, the angle at which the blade strikes the stenosis is effectively increased. As the atherectomy cutter has gradually become the procedure of preference in the treatment of stenoses, the need for a reliable manufacturing method has also developed. More specifically, because of the delicate nature of the atherectomy procedure, it is critical that the manufacturing process be reliable. Moreover, due to the small size of the atherectomy cutter, which may range in diameter from five to ten millimeters, it is necessary that the manufacturing process be completed while maintaining an extremely high level of precision.

In light of the above, it is an object of the present invention to provide a method for manufacturing an atherectomy cutter having a positive angle of attack. Another object of the present invention is to provide a method for manufacturing an atherectomy cutter which has superior cutting abilities. A further object of the present invention is to provide a method for manufacturing an atherectomy cutter which is reliable and maintains a high degree of precision. Yet another object of the present invention is to provide a method for manufacturing an atherectomy cutter for removing stenoses from a patient, which is relatively simple to follow, is easy to use, and is comparatively cost efficient.

SUMMARY OF THE INVENTION

The present invention pertains to a method for the manufacture of an atherectomy cutter having a positive angle of attack. To begin, a cutter blank is formed from a cylindrical rod. This rod inherently establishes the longitudinal axis for the cutter blank, and eventually, the longitudinal axis for the atherectomy cutter itself. Along this longitudinal axis, the cutter blank is formed with three contiguous coaxial sections. These are: a distal cylindrical section; a proximal cylindrical section; and a uniformly tapered section transitioning between the distal and proximal cylindrical sections. Importantly, the proximal cylindrical section has a larger diameter than the distal cylindrical section.

Following the formation of the cutter blank, walls of substantially similar thickness are created in each section of the cutter blank. Creation of the walls is accomplished by boring an axial passageway through the cutter blank from the distal end of the cutter blank to the proximal end of the cutter blank. More specifically, the proximal cylinder is bored to have an internal diameter slightly less than the external diameter of the proximal cylinder to create a tubular section. Similarly, the uniformly tapered section is bored with a tapered bore shaped to create walls of substantially the same thickness as the walls of the proximal cylindrical section. Finally, the distal cylinder is bored to have an internal diameter slightly less than the external diameter of the distal cylinder to create a tubular section with walls of substantially the same thickness as the two previous sections.

Following the creation of the axial passageway through the cutter blank, a pair of diametrically opposed flats are formed on the outer surface of the uniformly tapered section. Each flat is substantially planar and extends along the outer surface of the tapered section between the distal cylindrical section and the proximal cylindrical section.

After the formation of the flats on the outer surface of the uniformly tapered section, the walls of the uniformly tapered section between the flats are removed to create two diametrically opposed cutter blades. Additionally, a portion of the proximal cylinder immediately proximal and adjacent to the removed tapered section walls is also removed. Removal of the additional portion of the proximal cylinder results in the formation of a heel at the base of each of the cutter blades which connects the cutter blade to the proximal cylinder. Such wall removal is accomplished using electrical discharge machining, for example. Each cutter blade extends from the heel formed on the proximal cylinder to the distal cylinder, and is formed with a trapezoidal cross-section. More specifically, each blade has four sides: a flat; a first side surface; a second side surface which is opposite the first surface; and an inside surface which is opposite and smaller than the flat. The intersection of the flat and the first side surface defines the first cutting angle. Likewise, the intersection of the flat and the second side surface defines the second cutting angle. Consequently, during the removal of the wall portions of the uniformly tapered section immediately adjacent to the blades, particular attention is given to the formation of the cutting angle. This attention is given to insure that the angle between the flat and each side surface is less than approximately 60 degrees. In the event it is desirable to modify the cutting angle after formation of the cutter blank, the cutting angle may be changed by sharpening the blade.

BRIEF DESCRIPTION OF THE DRAWINGS

The novel features of the invention, as well as the invention itself, both as to its structure and its operation, will best be understood from the accompanying drawings, taken in conjunction with the accompanying description, in which similar reference characters refer to similar parts, and in which:

FIG. 1 is a block diagram showing the interrelation between the procedural steps of the present invention and the functional results obtained during that step;

FIG. 2 is a perspective view of a rod;

FIG. 7 is a cross-sectional view of the atherectomy cutter, as seen along line 7—7 of FIG. 6;

FIG. 8 is a cross-sectional view of a blade of an atherectomy cutter manufactured in accordance with the present invention as seen in the area designated 8—8 in FIG. 7; and FIG. 9 is a cross-sectional view of an atherectomy cutter in its intended operational environment.

DESCRIPTION OF THE PREFERRED EMBODIMENTS

According to the present invention, a method for manufacturing an atherectomy cutter having a positive angle of attack is presented. Referring initially to FIG. 1, it is to be appreciated that block diagram 10 shows a series of five steps which are to be performed in the manufacture of the atherectomy cutter. The manufacturing of an atherectomy cutter begins with first step 12 which requires the formation of a cutter blank 26.

Referring to FIG. 2, cylindrical rod 22 serves as the starting material from which cutter blank 26 is formed and, due to its shape, establishes the longitudinal axis 24. Cylindrical rod 22, however, is merely one shape and it is to be understood that material having any variety of shapes may be used.

In order to maintain orientation of the cutter blank 26 during this and following processes, cylindrical rod 22 may be inserted into a collet (not shown). The collet may be further retained in a collet holder (not shown) which will allow continuity of orientation when performing the required processes using a variety of machines.

Figure 3:
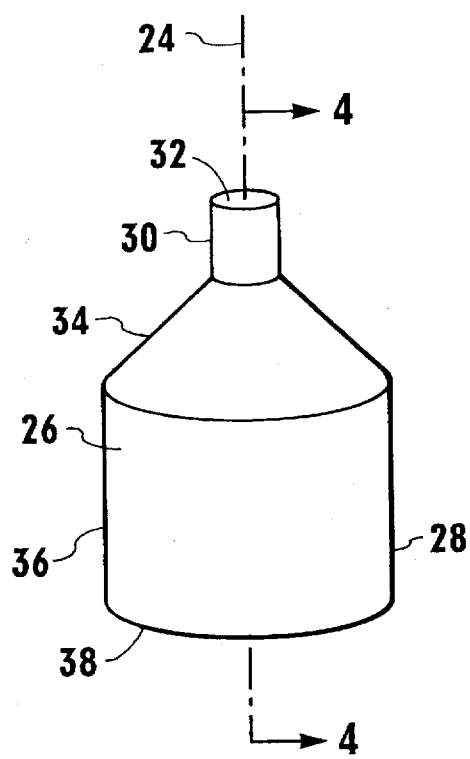
FIG. 3 is a perspective view of a cutter blank formed from the rod shown in FIG. 2.

Referring now to FIG. 3, cutter blank 26 is shown comprising three distinct sections which are each coaxial relative to longitudinal axis 24. These sections are: distal cylinder 30; proximal cylinder 36; and uniformly tapered section 34. As shown, the uniformly tapered section 34 transitions between distal cylinder 30 and proximal cylinder 36. Formation of a cutter blank 26, such as the one shown in FIG. 3, is easily accomplished using a lathe. A lathe, however, is merely exemplary, and any equivalent apparatus for forming metal rods which are known in the relevant art may be used.

Figure 4:
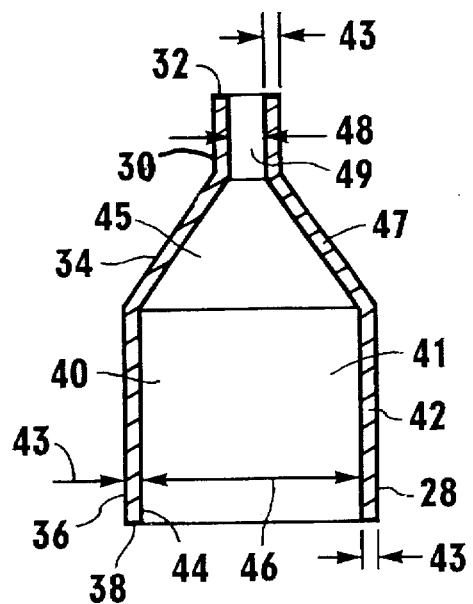
FIG. 4 is a cross-sectional view of a cutter blank formed with a passageway, as the blank would be seen along the line 4—4 in FIG. 3.

Referring back to block diagram 10 in FIG. 1, it is seen that following the formation of cutter blank 26 as required by first step 12, second step 14 requires the creation of an axial passageway 40 through cutter blank 26. Referring now to FIG. 4, it is shown that a bore 41 with a first diameter 46 has been created in proximal cylinder 36, leaving a wall 42, having a particular thickness 43. Further, it is seen that uniformly tapered section 34 has been bored with a tapered bore 45 to create a wall 47 of substantially similar thickness 43 to the wall 42 in proximal cylinder 36. Finally, FIG. 4 shows that a bore 49 with a second diameter 48 has been created in distal cylinder 30. Thus, cutter blank 26 now contains an axial passageway 40 from cutter blank proximal end 38 to cutter blank distal end 32. FIG. 4 also indicates that as a result of the creation of axial passageway 40, cutter blank 26 now has both an outer surface 28, and an inner surface 44.

Figure 5:
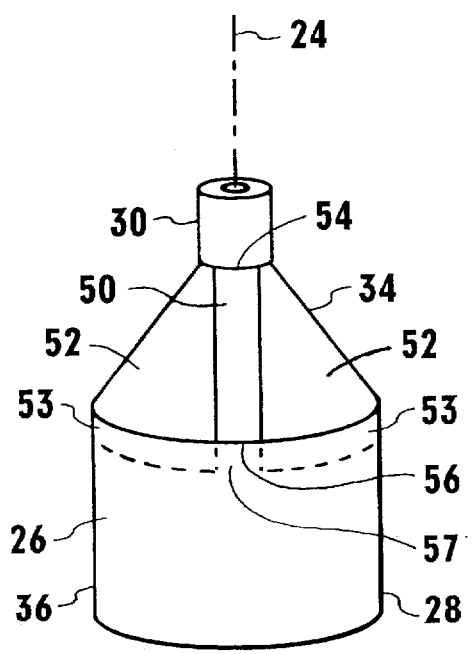
FIG. 5 is a perspective view of the cutter blank showing a flat.

Referring back to FIG. 1, it is seen that following second step 14, third step 16 requires the grinding of flats 50 on the outside surface of uniformly tapered section 34. Also, in FIG. 5, it can be seen that outer surface 28 of cutter blank 26 has been ground to create a flat 50. More specifically, in FIG. 5 it is shown that flat 50 has been ground on outer surface 28 of the uniformly tapered section 34 of cutter blank 26. From this view in FIG. 5, it is to be appreciated that there is a second flat 50 on the opposite side of cutter blank 26. Consequently, each cutter blank 26 has a pair of diametrically opposed flats 50. Each flat 50 is substantially planar and terminates at its proximal end 56 on the distal end of the proximal cylinder 36, and at its distal end 54 to the proximal end of the distal cylinder 30.

Referring back to FIG. 1, it is seen that following third step 16, fourth step 18 requires the removal of wall portions 52 of the uniformly tapered section 34, and an adjacent portion 53 of proximal cylinder 36 (shown by dashed lines), between flats 50 to create blades 60. Referring again to FIG. 5, flat 50 is shown separating wall portions 52. Moreover, it is to be appreciated that the removal of the wall portions 52 between flats 50, and adjacent portions 53 of proximal cylinder 36, would leave only the flats 50, the associated wall of uniformly tapered section 34, and connecting heel 57, to connect proximal cylinder 36 to distal cylinder 30.

Figure 6:
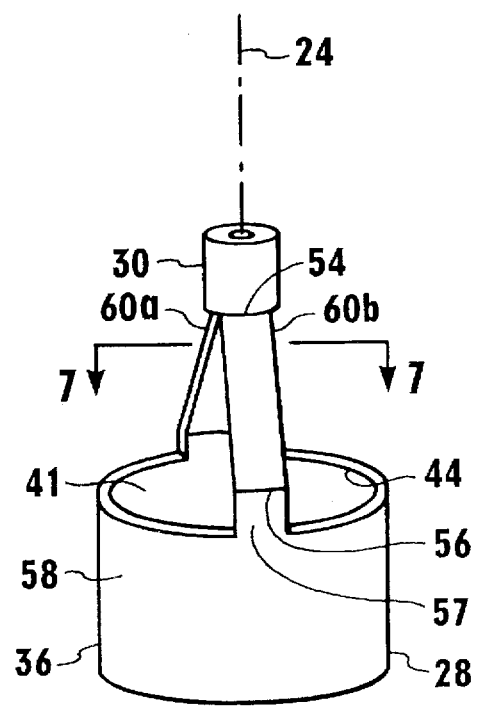
FIG. 6 is a perspective view of an atherectomy cutter formed from the cutter blank.

In FIG. 6, atherectomy cutter 58 is shown in perspective view. There, it is seen that following the removal of the uniformly tapered wall portions 52 and their adjacent portions 53, only flats 50 and connecting heels 57 remain to connect proximal cylinder 36 to distal cylinder 30. Thus, the combination of flats 50 and the associated wall 42 are collectively referred to as blades 60. From this figure, it can also be appreciated that by rotating atherectomy cutter 58 about its longitudinal axis 24, cutter blades 60 will generate a truncated conical cutting pattern. Also from this figure, it is seen that the removal of wall portions 52 provides for the viewing of the tubular nature of proximal cylinder 36, including inner surface 44 and the outer surface 28.

Note that particular attention is given to the removal of wall portions 52 immediately adjacent to flats 50 to insure precise formation of blades 60. To this end, removal of wall portions 52 may be accomplished by electrical discharge machining. Further, the electrical discharge machining may be accomplished using a formed electrode (not shown), and may even be accomplished while submerging the cutter blank and electrode in an dielectric fluid (not shown). Although not required, the shape of the formed electrode may be such that it conforms substantially with the shape of cutter blades 60. It is to be appreciated that electrical discharge machining is merely one manner of removing wall portions 52, and any method known in the art may be used.

FIG. 7 is a cross-sectional view of atherectomy cutter 50 and, similar to FIG. 6, shows bore 41 which creates the hollow cylindrical nature of proximal cylinder 36, including inside surface 44 and outside surface 28. Additionally, a cross-section of cutter blades 60 is shown as viewed from distal end 32 of the atherectomy cutter 58. Also readily visible from FIG. 6, and a critical feature of this atherectomy cutter, is the planar outer surface which form the flats 50 of cutter blades 60a and 60b.

The details of cutter blade 60a can be more readily seen in FIG. 8. Specifically, each of the cutter blades 60a,b has four sides. First, flat 50a represents the most lateral surface of the blade 60a, and as mentioned above, is a critical feature of this atherectomy cutter. Adjacent to flat 50a are first side surface 62, and second side surface 64. Inside surface 66 defines the inner surface of the cutting blade 60 and is bounded on both sides by first side surface 62 and second side surface 64. The intersection of first side surface 62 with flat 50 determines first cutting edge 68a and defines first cutting angle 70a, of the cutter blade 60a. Likewise, second cutting edge 68b is created by the intersection of second side surface 64 with flat 50, thereby defining second cutting angle 70b. Cutting angles 70a,b are critical to the operation of the atherectomy cutter 58 because they define the angle at which blade 60 will strike the stenosis 74. Consequently, it is important that blades 60 are precisely formed to create cutting angles 70a,b. Such precision is achieved using electrical discharge machining for the shaping of blades 60. Electrical discharge machining may also be used for formation of the cutting edges 70. More specifically, an electrical discharge machining electrode may be shaped to precisely conform with the cutting edge 70 to insure consistent and precise formation of cutting angle 70a,b. In this particular atherectomy cutter, less than approximately 60 degrees has been determined to be the optimal cutting angle 70a,b.

While FIG. 8 represents cutting angles 70a,b as substantially equal, such equality is not necessary. In fact, it may be useful to have different cutting angles 70a,b on the same atherectomy cutter 58 such that rotation of the cutter in one direction would utilize diametrically opposed cutting edges 68 on cutter blades 60a and 60b with a particular cutter angle 70, while rotation in the opposite direction would utilize cutting edges 68 having a different cutting angle 70. Despite the combination of cutting angles mentioned above, an even further combination of cutter angles 70 may be used, depending on the nature of the specific stenoses being excised.

Referring now back to FIG. 1, it is shown that following fourth step 18, fifth step 20 permits the sharpening of blades 50 to alter the cutting angle 70 of cutter blades 60. Referring again to FIG. 8, such sharpening would be used to perfect the cutting edge 68, but may also be used to increase or decrease the cutting angle 70 of blade 60. The sharpening of the blades 60 may be accomplished using lapping, and may further include lapping using progressively finer abrasives. Any method of sharpening known in the art, however, may be used to accomplish the same result.

In FIG. 9, atherectomy cutter 58 is shown in its natural environment, namely, inserted in artery 72 and positioned at stenosis 74. From this view, it can be appreciated that guide wire 78 can be inserted through both the distal cylinder 30 and proximal cylinder 36, along the longitudinal axis 24 of the atherectomy cutter 58, to guide the atherectomy cutter 58 through the artery 72. Further shown in this view, atherectomy cutter 58 can be mounted on torque tube 80 such that the atherectomy cutter 58 may be rotated along its longitudinal axis 24. By rotating atherectomy cutter 58, cutter blades 60 create a truncated conical cutting pattern and will strike the stenosis 74. Upon striking stenosis 74, cutter blades 60 will excise a portion of stenosis 74. By continually advancing the rotating atherectomy cutter 58 through stenosis 74, the entire stenosis 74 may be excised, thereby transforming the stenosis 74 into free floating stenotic particles 76. From this figure, it can further be appreciated that by applying a suction device (not shown) to the remote end of torque tube 80, stenotic particles 76 may be drawn into torque tube 80 and removed from the artery 72. Such removal of the stenotic particles 76 is particularly useful to insure that the particles will not travel through the artery 72, create another stenosis 74, and become a source of danger to the patient.

While the particular method for manufacturing an atherectomy cutter having a positive angle of attack as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A method for manufacturing an atherectomy cutter comprising the steps of:
    forming a cutter blank having a first cylinder with a first diameter a second cylinder with a second diameter, and a substantially uniformly tapered section therebetween;
    forming a passageway substantially through said cutter blank to create walls having a substantially similar thickness;
    creating a pair of substantially, diametrically opposed flats on said tapered section, each said flat having a proximal end, a distal end, and a substantially planar section therebetween; and
    removing said wall of said tapered section between said flats to create a plurality of blades, each said blade having at least one cutting edge defined by said flat and a respective side surface oriented at an angle from said flat.

2. A method for manufacturing, as recited in claim 1, wherein said angle between said flat and said respective side surface is less than approximately sixty degrees.

3. A method for manufacturing, as recited in claim 1, wherein the step of forming the cutter blank includes rotating the cutter blank about a cutter blank longitudinal axis.

4. A method for manufacturing, as recited in claim 1, wherein said step of removing said wall of said tapered section between said flats includes electrical discharge machining.

5. A method for manufacturing, as recited in claim 1, wherein said step of forming a passageway includes boring.

6. A method for manufacturing, as recited in claim 1, wherein said step of creating of substantially diametrically opposed flats includes grinding.

7. A method for manufacturing, as recited in claim 1, further comprising the removal of a portion of said first cylinder immediately proximal and adjacent to said removed wall of said tapered section, to form a heel for each said blade.

8. A method for manufacturing, as recited in claim 7, wherein said heels connect a respective said cutter blade to said first cylinder.

9. A method for manufacturing, as recited in claim 1, further comprising the step of sharpening said blades.

10. A method for manufacturing, as recited in claim 9, wherein the step of sharpening includes lapping.

11. A method for manufacturing, as recited in claim 10, wherein said lapping is performed using progressively finer abrasives.

12. A method for manufacturing, as recited in claim 9, wherein said sharpening includes grinding.

13. A method for manufacturing an atherectomy cutter comprising the steps of:
    providing a cutting blank having a tubular first section, a tubular second section, and a tubular tapered section which connects the first section to the second section;
    creating two spaced apart flats on the tapered section; and
    creating at least one blade by substantially removing the tapered section between at least two of the flats.

14. The method of claim 13 wherein the step of creating at least one blade includes the step of creating a plurality of blades by removing the tapered section between each of the flats.

15. The method of claim 13 wherein the step of creating at least one blade includes the step of creating at least one cutting edge defined by said flat and a respective side surface oriented at an angle from said flat.

* * * * *